United States Patent
Dahlke et al.

[11] Patent Number: 6,052,618
[45] Date of Patent: Apr. 18, 2000

[54] DEVICE FOR MAPPING ELECTRICAL ACTIVITY IN THE HEART

[75] Inventors: Mikael Dahlke, Trangsund; Leif Lindkvist, Stenhamra; Elisabeth Hjärne, Gustavsberg; Kjell Rasmundson, Uppsala; Börje Darpö, Saltsjö Duvnäs, all of Sweden

[73] Assignee: Siemens-Elema AB, Solna, Sweden

[21] Appl. No.: 09/109,390

[22] Filed: Jul. 2, 1998

[30] Foreign Application Priority Data

Jul. 11, 1997 [SE] Sweden ................... 9702678

[51] Int. Cl.[7] ................... A61B 5/044
[52] U.S. Cl. ................... 600/523; 600/509
[58] Field of Search ................... 600/509, 523, 600/513, 515, 407, 424, 436, 437, 525, 439, 463

[56] References Cited

U.S. PATENT DOCUMENTS

| | | | |
|---|---|---|---|
| 4,031,884 | 6/1977 | Henzel | 600/431 |
| 5,295,484 | 3/1994 | Marcus et al. | 600/439 |
| 5,433,198 | 7/1995 | Desai . | |
| 5,588,432 | 12/1996 | Crowley | 600/439 |
| 5,662,108 | 9/1997 | Budd et al. . | |
| 5,687,737 | 11/1997 | Branham et al. | 600/523 |
| 5,730,129 | 3/1998 | Darrow et al. | 600/407 |

*Primary Examiner*—Kennedy J. Schaetzle
*Attorney, Agent, or Firm*—Hill & Simpson

[57] ABSTRACT

A device for mapping electrical activity in a patient's heart, has an imaging unit, such as a fluoroscopic imaging unit, for generating a physical in vivo image of a patient's heart as an anatomical reference image, an electrode catheter, with at least one electrode for sensing intracardiac electrical activity, for insertion into a patient's heart, and signal processing equipment for determining activation times, from sensed electrical activity, in relation to a reference time for electrical activity at different points in the heart, and for generating a graphic image showing the activation times at different points in the heart and superimposing this graphic image onto the anatomical image. An arrangement is further provided for inserting at least one reference point into the anatomical image, and a setting unit moves the graphic image in relation to the reference image with the aid of the reference point.

13 Claims, 4 Drawing Sheets

DEVICE FOR MAPPING ELECTRICAL ACTIVITY IN THE HEART

BACKGROUND OF THE INVENTION

1. Field of the Invention

The present invention relates to a device for mapping in vivo electrical activity in a heart.

2. Description of the Prior Art

Devices for mapping electrical activity in a patient's heart are known which include an imaging unit for generating an anatomical reference image of a patient's heart, an electrode catheter with at least one electrode for sensing intracardiac electrical activity for insertion into the heart, and signal processing equipment for determining activation times, from sensed electrical activity, in relation to a reference time for electrical activity at different points in the heart, and for generating a graphic image showing the activation times at different points in the heart and superimposing this graphic image onto the anatomical image.

One general problem in this type of electrophysiological studies is to correlate information measured in time to the anatomical structure of the heart. For this purpose, a common method is to apply a transparent film to a fluoroscope monitor, to "freeze" the image for every time sample, and to manually enter time data at the position of the electrode catheter's tip on the monitor. The tip of the catheter is then moved to a new position, and the procedure is repeated until an isochronous image is obtained.

Time data, e.g. in the form of activation times in relation to a reference time at different points in heart tissue, can be translated into colors in order to achieve color-coded representation of time information.

A device of the initially described type is previously known from U.S. Pat. No. 5,433,198 which describes a system for such cardiomapping, whereby received information is utilized for treating tachycardia with ablation. Thus, the system according to this patent has an imaging unit which, via a detector, generates an anatomical image of the heart on a monitor. The imaging unit is fluoroscopic or ultrasonic. With multi-electrode catheters connected to appropriate signal processing equipment, a real-time image is generated of arrival times of a characteristic signal at different points in the heart with respect to a reference time and local isochronous images are displayed on the monitor, from which the origin of a tachycardia can be identified.

SUMMARY OF THE INVENTION

An object of the present invention is to provide a cardiomapping device which correlates, in a new and reliable manner, time information received in mapping to the anatomical structure of the heart.

In a device according to the invention, a graphic image of activation times at different points in the heart is superimposed on an anatomical image, obtained using a source of radiation which may, for example, generate one or other of ultrasound or x-rays. The generation of a reference point and a setting arrangement ensure that the graphic image is correctly aligned in relation to the anatomical image. This is of the greatest importance if the patient e.g. moves between measurements and if the operator wishes to revert to a previous position for e.g. ablation treatment.

In an embodiment of the device according to the invention, reference means are arranged to insert a reference point, corresponding to the reference point in the anatomical image, into the graphic image. The graphic image can therefore be oriented on the anatomical image when these reference points are aligned with each other. In an initial exposure, certain reference points, or landmarks, are accordingly set, and the graphic image is aligned with these reference points for every subsequent measurement, thereby ensuring that every sampled time value is assigned to the correct position in the anatomical image. The superimposed image and the anatomical image also make it easier for the operator, guided by the image of the patient's unique anatomy, to position the catheter.

According to another embodiment of the inventive device, the anatomical image and the graphic image including measured electrical activity are stored in an electronic memory connected to the setting means. The setting means move the graphic image in the memory, according to stored information, until reference points in the anatomical image and the graphic image coincide when the graphic image is superimposed on the anatomical image. This therefore achieves automatic positioning of the graphic image on the anatomical image.

In a further embodiment of the device according to the invention, the imaging unit and the signal processing equipment are arranged to generate superimposed images in more than one projection. Two projections are used if a fluoroscopic imaging system is e.g. a biplane system.

In another embodiment of the device according to the invention in which the imaging unit comprises a source of radiation for generating an image of the patient's heart and a detector for detecting that image, the source of radiation and detector being moveable in relation to each another and to the patient, information can be stored in the memory on the angular positions of the source of radiation and detector, in relation to the patient table, as well as information on the distance between the source of radiation and the table. When information on angle and table height is stored with the current image, automatic magnification information is obtained. The operator is then always able to revert to a previous projection after the source of radiation and detector have been moved.

In another embodiment of the device according to the invention, the signal processing equipment is correlated to the IEGM recorded during the measurement so activation times are determined in the same phase of the heart cycle. A breathing sensor can be provided for sensing the patient's breathing and cause the signal processing equipment to correlate determination of activation time to the patient's breathing, e.g. so the time is always determined in the same phase of breathing.

In a further embodiment of the device according to the invention, a color generator translates numerical values for activation times into a color-coded image for superimposition onto the anatomical image. A glance at the composite image then gives the operator an immediate overview of the propagation of electrical activity in the patient's heart.

In another embodiment of the device according to the invention, the electrode catheter is arranged for connection to ablation equipment for performing ablation. Here, the signal processing equipment is appropriately arranged to display in the graphic image information on ablation, such as the present position of the catheter in the heart, the time ablation is performed, the effect of ablation etc.

DESCRIPTION OF THE PREFERRED EMBODIMENTS

Figure 1:
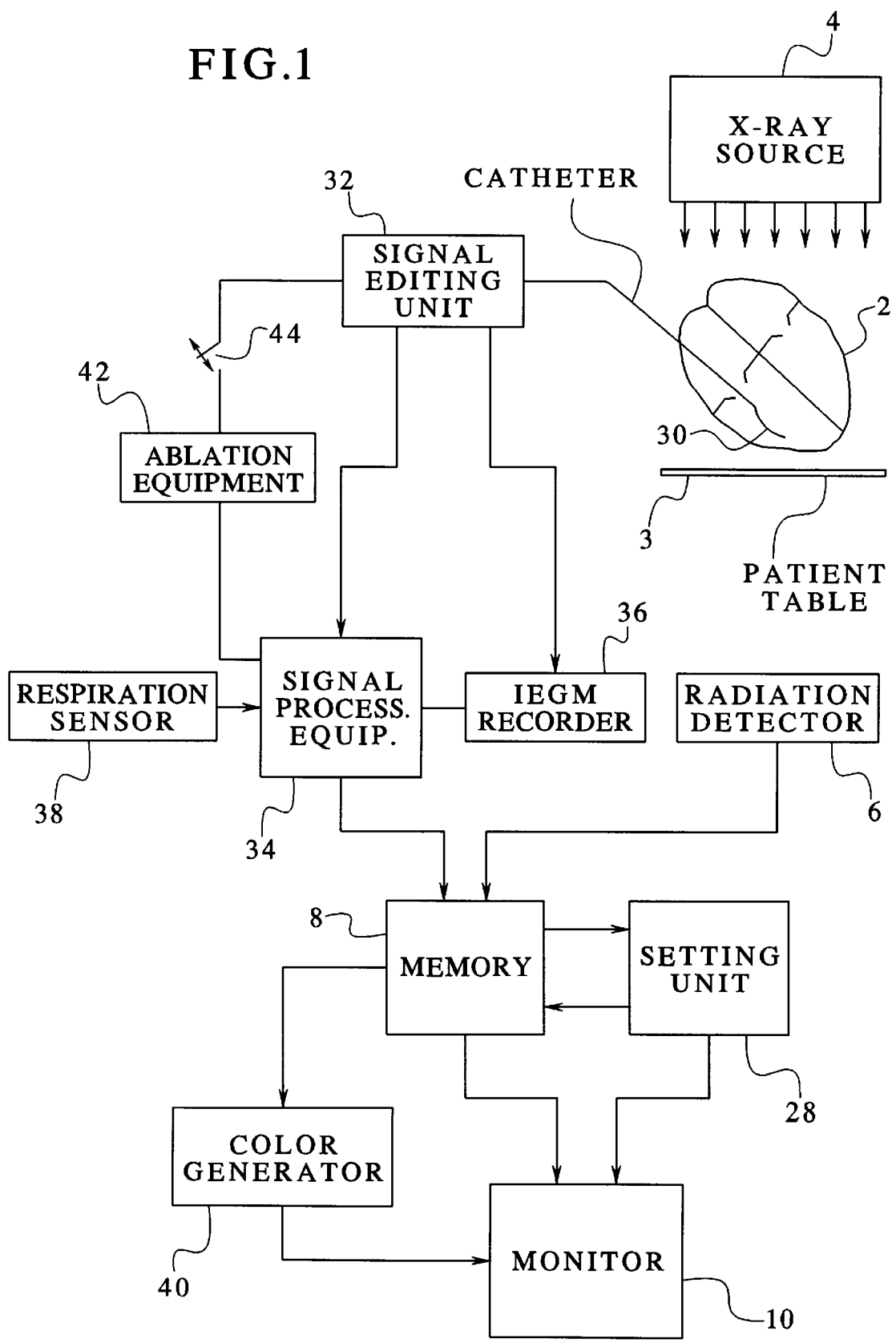
FIG. 1 is a block diagram illustrating one embodiment of the device according to the invention.

The embodiment of the device according to the invention shown in FIG. 1 has an imaging unit for generating an anatomical fluoroscopic image of a heart 2 of a patient on a patient table 3. The imaging unit includes a an x-ray source 4 and a detector 6 for detecting the radiographic image. The detected image is sent to a memory 8, whose function will be described in greater detail below, and to a monitor 10 for displaying the image.

It would be advantageous if information on the angular positions of the x-ray source 4 and the detector 6 in relation to the patient table 3, as well as information on the distance between the x-ray source 4 and the table 3 and/or the detector 6, could also be stored with the image in the memory 8. If the x-ray source 4 and the detector 6 are arranged on a stand, e.g. on a C-arm, their angular positions in relation to the patient table 3 and the distance between the x-ray source 4 and detector 6 can be varied when their position is shifted along the arm. This information about the angular position on the arm, plus information on the height of the patient table 3, is needed to enable an operator to return the x-ray source 4 and the detector 6 to a specific, previous position. Since this information about angle and distance can be stored in the memory 8 along with the current image, improved functionality is achieved for the device according to the invention, including e.g. automatic magnification.

Figure 2:
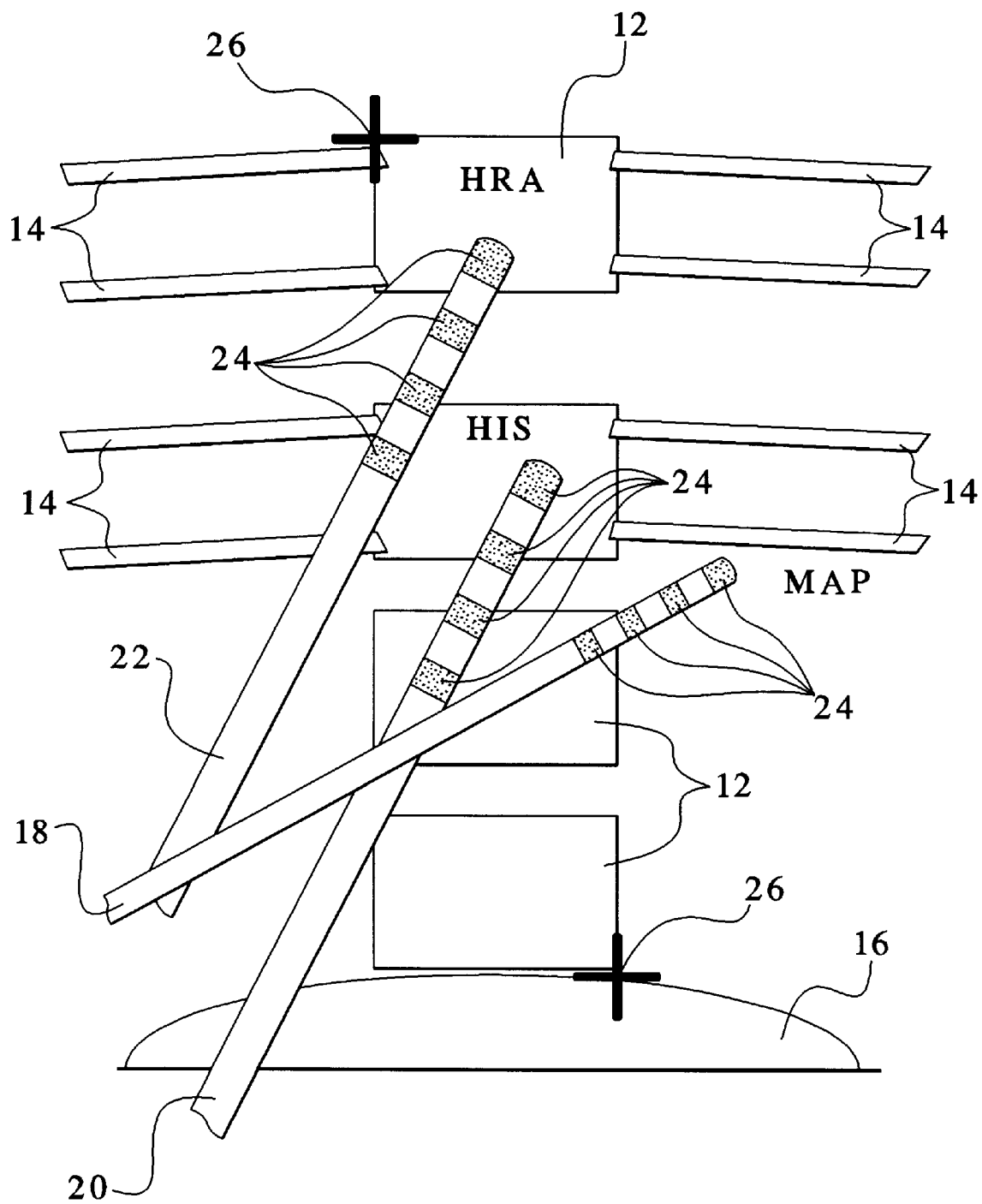
FIGS. 2–4 show stylized radiographs of the chest with inserted reference points, electrode catheters at different positions and representation of measurement values obtained using the inventive device.
Figure 3:
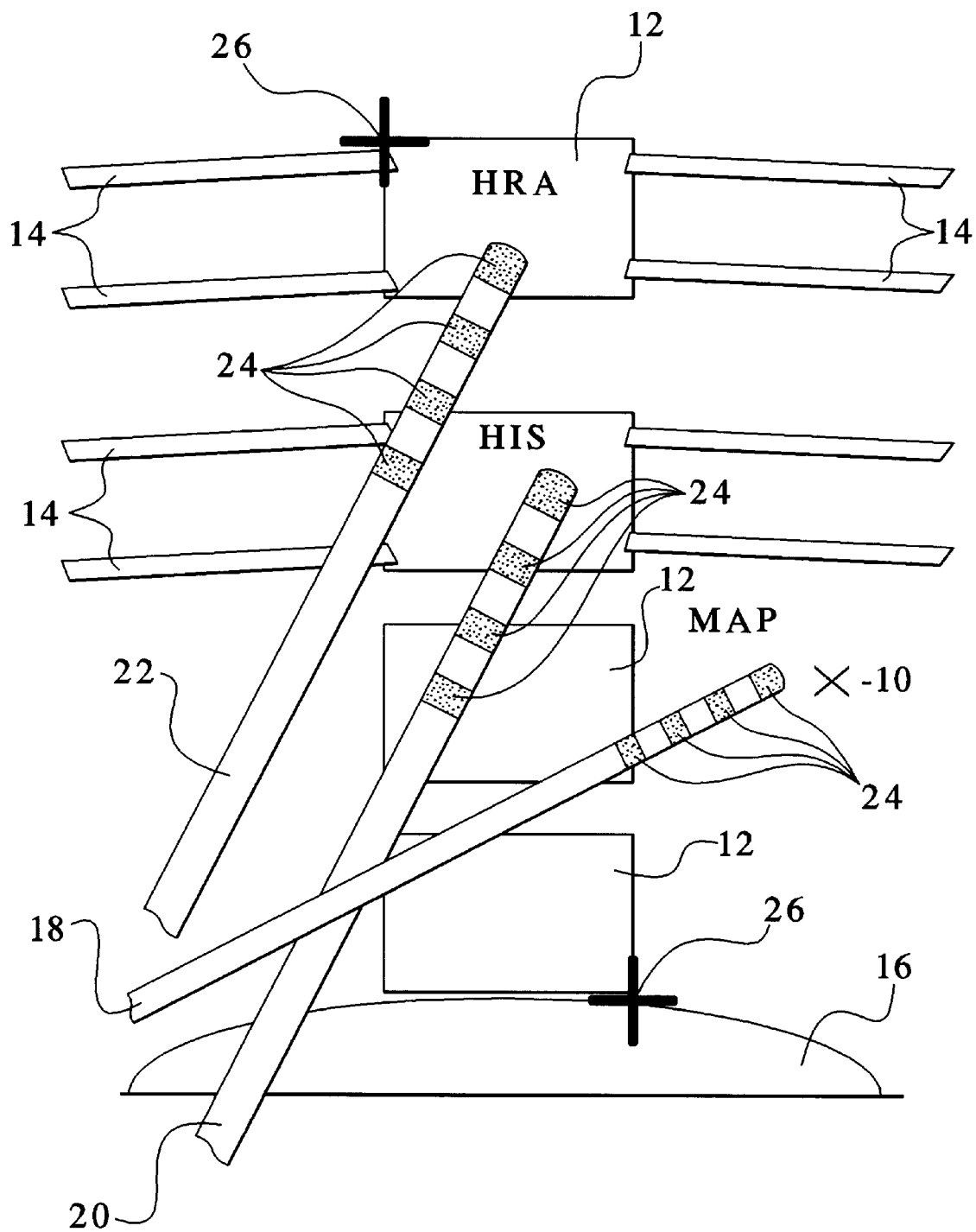
Figure 4:
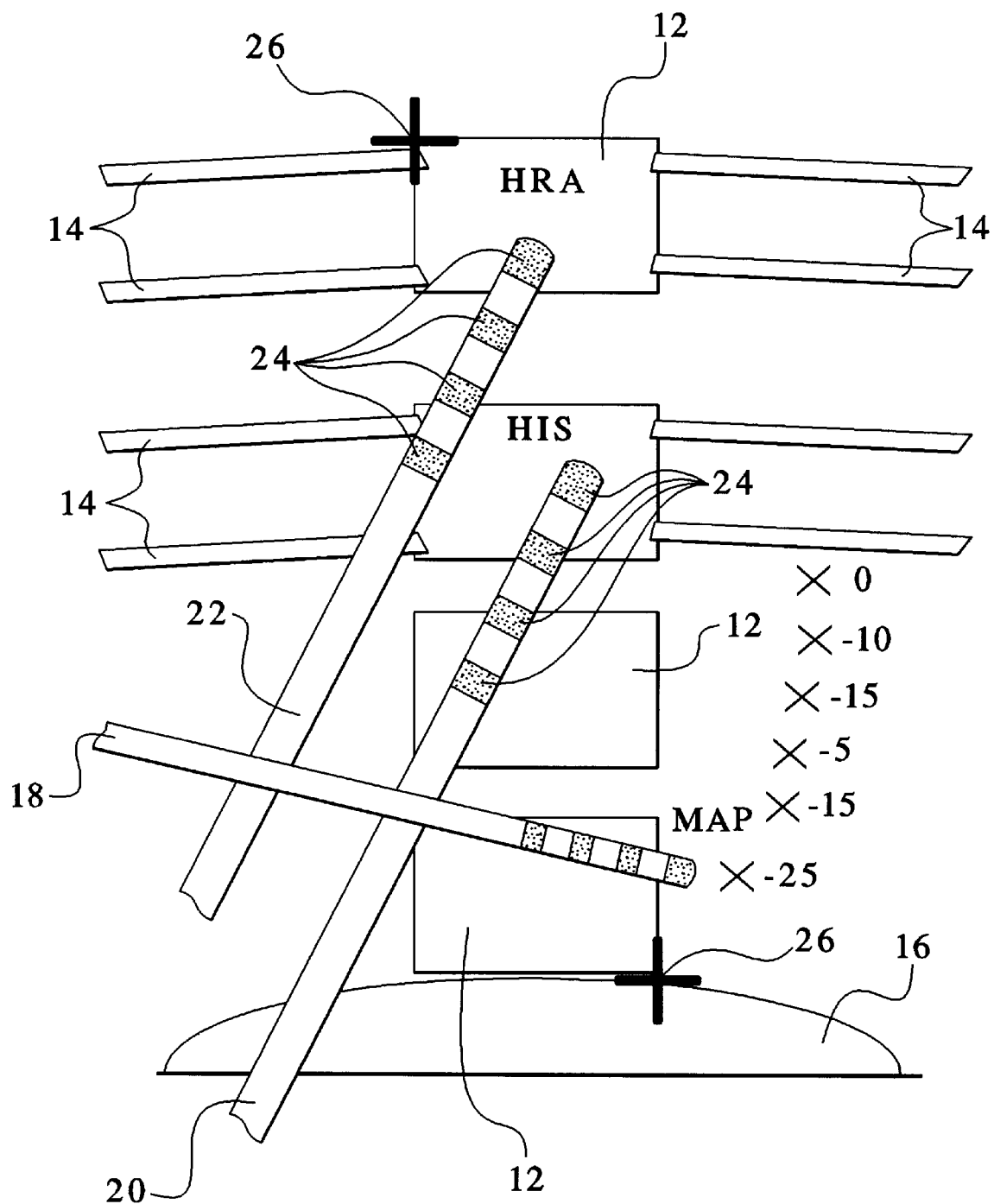

Stylized radiographs of the chest made with the device according to the invention are shown in FIGS. 2–4. In this type of image, the heart appears, at best, as a pale shadow. The heart is not shown at all in these figures. The body parts seen most clearly in the radiograph are skeletal parts, such as spinal vertebrae 12 and ribs 14. The diaphragm, suggested at 16, is depicted normally in these images, and the electrodes 24 of the electrode catheters 18, 20, 22 are clearly seen. Typical catheter positions are marked in the images, viz. HRA=high right atrium, HIS=bundle of His and MAP=mapping catheter. In practice, the catheter 18, 20, 22 to be used for measurement can be selected when an operator clicks on the desired catheter 18, 20, 22 in the monitor image.

The first radiograph (FIG. 2), is saved as a reference, and a reference marking 26 is inserted at one or a number of points in the image. In practice, the reference points 26 are selected when the operator clicks with a mouse on the desired points in the reference image on the monitor 10. In FIGS. 2–4, the transition between a spinal vertebra 12 and a rib 14 is used as one reference mark, and the transition between a 20 spinal vertebrae 12 and the diaphragm 16 is used as a second reference mark.

The image in FIG. 3 is used for the second point for measurement of electrical activity in the heart. Here, the image is adjusted, first vertically and then horizontally, until the reference points 26 are aligned with the positions shown in the image in FIG. 2. This can be performed manually by moving the x-ray table with the patient on it or automatically when the image is "moved" in the memory 8 (see FIG. 1). The reference image is stored in the memory 8. When the new image is stored in the memory 8, an offset can be calculated and sent to the setting unit 28 which makes the necessary adjustments so the electrical activation measured with the electrode catheter 18 is displayed on the monitor 10 in ms, related to the first reference measurement according to FIG. 2. In a measurement according to FIG. 3, the time of the measured electrical activation is shown as −10. The minus sign designates that activation at the current measurement point occurs before activation in the reference measurement. The measurement value and its position are stored with the IEGMs simultaneously recorded with the electrode catheter(s) 30.

A signal other than MAP in FIG. 2, e.g. HRA, can be used as a reference.

FIG. 4 shows an image with an additional number of measurements. For clarity, only five measurement points are shown, however, many more measurements are made in reality, i.e. normally 15–30, and a number of measurements can be made simultaneously. As in FIG. 3, the minus sign indicates that the measured activation occurred before activation at the reference point, and the source of a tachycardia can be located with the aid of this additional information.

Thus, activation times measured with the mapping catheter and their locations in the anatomical image are displayed in the image.

The signal picked up by the electrode catheter 30 is sent, after preconditioning at in a signal editing unit to signal processing equipment 34. The signal is also sent to an IEGM recorder 36 for recording IEGMs, and the IEGM information is also sent to the signal processing equipment 34. Recorded IEGMs are sent to the signal processing equipment 34 so measurements can be triggered by the IEGM, causing measurements to be performed in the same phase of every heart cycle. Alternatively, measurement for the same purpose can be triggered by a recorded surface ECG.

The ensuing output signal from signal processing equipment 34 is sent to the memory 8 for presentation in the corresponding radiographic image on the monitor 10.

A respiration sensor 38 can similarly be appropriately connected to the signal processing equipment 34 to sense the patient's breathing and cause the signal processing equipment 34 to perform measurements in a specific phase of the patient's breathing cycle.

The device according to the invention can be devised to perform the measurement in one or a number of projections. The most common projections are LAO (left anterior oblique) and RAO (right anterior oblique). With mapping in different projections, information about the angular positions of the x-ray source 4 and detector 6 in relation to the patient table 3, as well as information about the distance between the x-ray source 4 and the patient table 3 and/or the detector 6, must be stored with the relevant image, as described above.

Measurement values are displayed numerically in FIGS. 2–4, however, a color generator 40 can be arranged to translate numerical values for activation times into a color-coded image for superimposition on the anatomical x-ray image. A color-coded image gives the operator an immediate overview of the heart's electrical activation.

The device according to the invention can also include ablation equipment 42 which is connectable to the electrode catheter 30 by a switch 44. In ablation the ability to return the catheter 30 to a specific ablation position is often desirable. This can be simply and reliably achieved with the device according to the invention with the aid of reference marks 26 in the image. Here, the catheter positions at which ablation has been performed are displayed, and information about energy and time, as well the effect of the ablation on the arrhythmia being treated, e.g. "no effect", "tachycardia terminated", "transient tachycardia" etc., can be linked to these points.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for mapping in vivo electrical activity of a heart, comprising:

an imaging unit which generates an anatomical reference image comprising an in vivo physical image of a heart disposed in a patient;

a catheter carrying at least one electrode for sensing intracardiac electrical activity, said catheter being adapted for insertion into a heart;

signal processing means for determining activation times, from electrical activity sensed by said at least one electrode, in relation to a reference time for electrical activity at different points in a heart;

means for generating a graphic image showing said activation times at said different points in the heart and for superimposing said graphic image onto said anatomical reference image;

reference means for inserting at least one reference point into said anatomical reference image; and setting means for aligning said graphic image with said anatomical reference image dependent on said reference point.

2. A device as claimed in claim 1 wherein said reference means comprises means for inserting a graphic image reference point into said graphic image corresponding to said reference point in said anatomical reference image.

3. A device as claimed in claim 2 comprising an electronic memory connected to said setting means for storing said anatomical reference image and said graphic image and said measured electrical activity, and wherein said setting means comprises means for arranging said graphic image in said memory so that said reference point in said anatomical reference image and said graphic image reference point are aligned.

4. A device as claimed in claim 1 wherein said reference means comprises means for inserting first and second reference points in said anatomical reference image and for inserting first and second graphic image reference points into said graphic image, and wherein said setting means comprises means for aligning said first reference point in said anatomical reference image with said first graphic image reference point and for aligning said second reference point in said anatomical reference image with said second graphic image reference point to align said graphic image with said reference image.

5. A device as claimed in claim 1 wherein said imaging unit and said signal processing means comprise means for generating superimposed images in more than one projection.

6. A device as claimed in claim 1 wherein said imaging unit comprises a radiation source and a radiation detector for detecting radiation from said radiation source attenuated by a heart, means for moving said radiation source and said detector relative to each other and relative to a patient, a patient table adapted to receive a patient thereon, and memory means for storing information during generation of said anatomical reference image regarding angular positions of said radiation source and said detector relative to said patient table 3, and information identifying a distance between said radiation source and said patient table.

7. A device as claimed in claim 1 wherein said intracardiac electrical activity comprises an IEGM identifying a succession of heart cycle phases, and wherein said signal processing means comprises means for identifying said activation times in a same phase of each heart cycle.

8. A device as claimed in claim 1 further comprising a respiration sensor which produces electrical signals representative of a respiration cycle of a patient, said electrical signals being supplied to said signal processing means, and wherein said signal processing means comprises means for identifying said activation times in a same phase of each respiration cycle.

9. A device as claimed in claim 1 wherein said activation times have numerical values associated therewith, and said device further comprising color generator means for translating said numerical values into a color-coded image for superimposition on said anatomical reference image as said graphic image.

10. A device as claimed in claim 1 further comprising ablation equipment, connected to said electrode catheter, for performing ablation dependent on said anatomical reference image and said graphic image.

11. A device as claimed in claim 10 wherein said signal processing means comprises means for displaying ablation information in said graphic image.

12. A device as claimed in claim 11 wherein said signal processing means comprises means for displaying ablation information selected from the group consisting of a position of said catheter in a heart, a time ablation was performed, and an effect of the ablation.

13. A device as claimed in claim 1 wherein said imaging unit comprises means for generating a fluoroscopic image as said anatomical image.

* * * * *